(12) United States Patent
Horgan et al.

(10) Patent No.: US 10,456,283 B2
(45) Date of Patent: Oct. 29, 2019

(54) APPARATUS AND METHOD FOR MAINTAINING PATENCY IN A VESSEL ADJACENT TO NEARBY SURGERY

(71) Applicant: BOSTON SCIENTIFIC SCIMED, INC., Maple Grove, MN (US)

(72) Inventors: Fergal Horgan, Co. Mayo (IE); Adrian McNamara, Galway (IE); Fionnuala O'Gorman, Dublin (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 189 days.

(21) Appl. No.: 15/648,670

(22) Filed: Jul. 13, 2017

(65) Prior Publication Data

US 2018/0014956 A1    Jan. 18, 2018

Related U.S. Application Data

(60) Provisional application No. 62/361,655, filed on Jul. 13, 2016.

(51) Int. Cl.
| | |
|---|---|
| *A61F 2/95* | (2013.01) |
| *A61F 2/844* | (2013.01) |
| *A61F 2/24* | (2006.01) |
| *A61M 25/04* | (2006.01) |

(52) U.S. Cl.
CPC .............. *A61F 2/95* (2013.01); *A61F 2/2427* (2013.01); *A61F 2/844* (2013.01); *A61F 2002/9522* (2013.01); *A61F 2002/9528* (2013.01); *A61F 2250/0003* (2013.01); *A61M 25/04* (2013.01)

(58) Field of Classification Search
CPC .......... A61F 2/844; A61F 2/95; A61F 2/2427; A61F 2002/9522; A61F 2250/0003; A61F 2002/9528; A61M 25/04
See application file for complete search history.

(56) References Cited

U.S. PATENT DOCUMENTS

| | | | |
|---|---|---|---|
| 4,545,390 A | 10/1985 | Leary | |
| 4,601,705 A | 7/1986 | McCoy | |
| 4,650,466 A | 3/1987 | Luther | |
| 4,777,951 A | 10/1988 | Cribier et al. | |
| 4,819,751 A | 4/1989 | Shimada et al. | |
| 4,986,830 A | 1/1991 | Owens et al. | |
| 5,041,093 A | 8/1991 | Chu | |
| 5,222,971 A | 6/1993 | Willard et al. | |
| 5,309,896 A * | 5/1994 | Moll ............... | A61B 17/00234 128/898 |
| 5,449,372 A | 9/1995 | Schmaltz et al. | |
| 5,554,181 A * | 9/1996 | Das ......................... | A61F 2/82 606/194 |

(Continued)

FOREIGN PATENT DOCUMENTS

CA    2747940 A1    2/2013

OTHER PUBLICATIONS

International Search Report and Written Opinion dated Sep. 26, 2017 for International Application No. PCT/US2017/041896.

*Primary Examiner* — Phong Son H Dang
(74) *Attorney, Agent, or Firm* — Seager, Tufte & Wickhem LLP

(57) ABSTRACT

The disclosure pertains to an apparatus for maintaining patency within vessels in the vicinity of surgical procedures which might otherwise be compressed and partially or totally occluded and methods of use therefor.

6 Claims, 10 Drawing Sheets

(56) References Cited

U.S. PATENT DOCUMENTS

| | | | |
|---|---|---|---|
| 5,626,602 A | 5/1997 | Gianotti et al. | |
| 5,906,590 A | 5/1999 | Hunjan et al. | |
| 5,980,533 A * | 11/1999 | Holman | A61F 2/95 606/191 |
| 6,013,019 A | 1/2000 | Fischell et al. | |
| 6,027,516 A | 2/2000 | Kolobow et al. | |
| 6,059,752 A | 5/2000 | Segal | |
| 6,066,149 A | 5/2000 | Samson et al. | |
| 6,162,237 A | 12/2000 | Chan | |
| 6,187,054 B1 | 2/2001 | Colone et al. | |
| 6,231,598 B1 * | 5/2001 | Berry | A61L 31/022 623/1.15 |
| 6,368,344 B1 * | 4/2002 | Fitz | A61F 2/95 606/108 |
| 6,383,205 B1 | 5/2002 | Samson et al. | |
| 6,398,758 B1 | 6/2002 | Jacobsen et al. | |
| 6,458,151 B1 | 10/2002 | Saltiel | |
| 6,494,907 B1 | 12/2002 | Bulver | |
| 6,514,273 B1 | 2/2003 | Voss et al. | |
| 6,540,768 B1 | 4/2003 | Diaz et al. | |
| 6,562,064 B1 | 5/2003 | deBeer | |
| 6,572,648 B1 | 6/2003 | Klumb et al. | |
| 6,616,689 B1 * | 9/2003 | Ainsworth | A61F 2/915 623/1.15 |
| 6,645,237 B2 | 11/2003 | Klumb et al. | |
| 6,660,032 B2 | 12/2003 | Klumb et al. | |
| 6,673,042 B1 | 1/2004 | Samson et al. | |
| 6,921,414 B2 | 7/2005 | Klumb et al. | |
| 6,991,641 B2 | 1/2006 | Diaz et al. | |
| 7,004,954 B1 | 2/2006 | Voss et al. | |
| 7,128,752 B2 | 10/2006 | Bales | |
| 7,618,432 B2 | 11/2009 | Pedersen et al. | |
| 7,744,620 B2 | 6/2010 | Pedersen et al. | |
| 7,766,871 B2 | 8/2010 | Hirszowicz et al. | |
| 7,875,050 B2 | 1/2011 | Samson et al. | |
| 7,931,664 B2 | 4/2011 | Gray | |
| 7,951,111 B2 | 5/2011 | Drasler et al. | |
| 7,951,186 B2 | 5/2011 | Eidenschink et al. | |
| 7,996,993 B2 | 8/2011 | Gray | |
| 8,057,396 B2 | 11/2011 | Forster et al. | |
| 8,066,757 B2 | 11/2011 | Ferrera et al. | |
| 8,070,791 B2 | 12/2011 | Ferrera et al. | |
| 8,088,140 B2 | 1/2012 | Ferrera et al. | |
| 8,100,935 B2 | 1/2012 | Rosenbluth et al. | |
| 8,192,479 B2 | 6/2012 | Paul, Jr. | |
| 8,197,493 B2 | 6/2012 | Ferrera et al. | |
| 8,361,016 B2 | 1/2013 | Siegel et al. | |
| 8,366,737 B2 | 2/2013 | Hancock et al. | |
| 8,406,867 B2 | 3/2013 | Kassab | |
| 8,460,368 B2 | 6/2013 | Taylor et al. | |
| 8,486,014 B2 | 7/2013 | Kelly et al. | |
| 8,486,025 B2 | 7/2013 | Solar et al. | |
| 8,486,102 B2 | 7/2013 | Pedersen et al. | |
| 8,486,104 B2 | 7/2013 | Samson et al. | |
| 8,491,614 B2 | 7/2013 | LeMaitre et al. | |
| 8,574,247 B2 | 11/2013 | Adams et al. | |
| 8,574,262 B2 | 11/2013 | Ferrera et al. | |
| 8,585,594 B2 | 11/2013 | Forster et al. | |
| 8,585,713 B2 | 11/2013 | Ferrera et al. | |
| 8,623,074 B2 | 1/2014 | Ryan | |
| 8,632,559 B2 | 1/2014 | Gershony et al. | |
| 8,652,099 B2 | 2/2014 | Fierens et al. | |
| 8,679,142 B2 | 3/2014 | Slee et al. | |
| 8,709,075 B2 | 4/2014 | Adams et al. | |
| 8,784,467 B2 | 7/2014 | Connelly et al. | |
| 8,784,480 B2 | 7/2014 | Taylor et al. | |
| 8,808,237 B2 | 8/2014 | Thielen et al. | |
| 8,828,040 B2 | 9/2014 | Goff | |
| 8,900,264 B2 | 12/2014 | Drasler et al. | |
| 8,926,680 B2 | 1/2015 | Ferrera et al. | |
| 8,945,143 B2 | 2/2015 | Ferrera et al. | |
| 8,945,172 B2 | 2/2015 | Ferrera et al. | |
| 9,005,139 B2 | 4/2015 | Klaiman et al. | |
| 9,034,025 B2 | 5/2015 | Sanati et al. | |
| 9,044,618 B2 | 6/2015 | Hawkins et al. | |
| 9,044,619 B2 | 6/2015 | Hawkins et al. | |
| 9,050,441 B2 | 6/2015 | Solar et al. | |
| 9,161,834 B2 | 10/2015 | Taylor et al. | |
| 9,198,687 B2 | 12/2015 | Fulkerson et al. | |
| 9,216,082 B2 | 12/2015 | Von Segesser et al. | |
| 9,220,521 B2 | 12/2015 | Hawkins et al. | |
| 9,232,961 B2 | 1/2016 | LeMaitre et al. | |
| 9,242,081 B2 | 1/2016 | Drasler et al. | |
| 9,289,224 B2 | 3/2016 | Adams et al. | |
| 9,289,581 B2 | 3/2016 | Magnuson et al. | |
| 9,339,230 B2 | 5/2016 | Kassab | |
| 9,351,756 B2 | 5/2016 | Gershony et al. | |
| 9,364,254 B2 | 6/2016 | Gershony et al. | |
| 9,375,555 B2 | 6/2016 | Pedersen et al. | |
| 9,387,098 B2 | 7/2016 | Ferrera et al. | |
| 9,414,852 B2 | 8/2016 | Gifford, III et al. | |
| 9,421,025 B2 | 8/2016 | Hawkins et al. | |
| 9,445,829 B2 | 9/2016 | Brady et al. | |
| 9,480,823 B2 | 11/2016 | Roche et al. | |
| 9,486,188 B2 | 11/2016 | Secrest et al. | |
| 9,504,807 B2 | 11/2016 | Drasler et al. | |
| 9,545,323 B2 | 1/2017 | Cully | |
| 10,195,014 B2 * | 2/2019 | Lamson | A61B 17/0401 |
| 2001/0020173 A1 | 9/2001 | Klumb et al. | |
| 2001/0020182 A1 | 9/2001 | Klumb et al. | |
| 2001/0044621 A1 | 11/2001 | Klumb et al. | |
| 2001/0051822 A1 * | 12/2001 | Stack | A61F 2/91 623/1.11 |
| 2002/0077693 A1 | 6/2002 | Barclay et al. | |
| 2003/0028245 A1 | 2/2003 | Barclay et al. | |
| 2003/0225444 A1 | 12/2003 | Klumb et al. | |
| 2004/0122466 A1 | 6/2004 | Bales | |
| 2004/0153142 A1 | 8/2004 | Klumb et al. | |
| 2004/0220604 A1 | 11/2004 | Fogarty et al. | |
| 2005/0060025 A1 * | 3/2005 | Mackiewicz | A61F 2/91 623/1.34 |
| 2005/0165412 A1 | 7/2005 | Secrest et al. | |
| 2005/0273147 A1 | 12/2005 | Israel | |
| 2006/0020324 A1 * | 1/2006 | Schmid | A61F 2/856 623/1.16 |
| 2006/0136033 A1 | 6/2006 | Hermann et al. | |
| 2006/0136034 A1 | 6/2006 | Modesitt et al. | |
| 2006/0136035 A1 | 6/2006 | Hermann et al. | |
| 2006/0206125 A1 | 9/2006 | Fogarty et al. | |
| 2006/0235506 A1 * | 10/2006 | Ta | A61F 2/91 623/1.16 |
| 2006/0282152 A1 * | 12/2006 | Beyerlein | A61F 2/95 623/1.11 |
| 2007/0016243 A1 | 1/2007 | Ramaiah et al. | |
| 2007/0173923 A1 * | 7/2007 | Savage | A61F 2/91 623/1.15 |
| 2007/0219616 A1 | 9/2007 | Modesitt et al. | |
| 2007/0239259 A1 * | 10/2007 | Boylan | A61F 2/91 623/1.15 |
| 2007/0293930 A1 * | 12/2007 | Wang | A61F 2/91 623/1.11 |
| 2008/0058856 A1 | 3/2008 | Ramaiah et al. | |
| 2008/0114439 A1 | 5/2008 | Ramaiah et al. | |
| 2008/0125848 A1 * | 5/2008 | Kusleika | A61L 29/02 623/1.11 |
| 2010/0070015 A1 * | 3/2010 | Schneider | A61F 2/95 623/1.11 |
| 2010/0160951 A1 | 6/2010 | Madison | |
| 2010/0318097 A1 | 12/2010 | Ferrera et al. | |
| 2011/0082490 A1 | 4/2011 | Connelly et al. | |
| 2012/0046678 A1 | 2/2012 | LeMaitre et al. | |
| 2012/0259400 A1 * | 10/2012 | Von Oepen | A61F 2/86 623/1.11 |
| 2012/0271409 A1 * | 10/2012 | Bruszewski | A61F 2/07 623/1.34 |
| 2013/0267974 A1 | 10/2013 | LeMaitre et al. | |
| 2014/0214148 A1 * | 7/2014 | Shokoohi | A61F 2/95 623/1.12 |
| 2016/0100855 A1 | 4/2016 | LeMaitre et al. | |
| 2018/0071120 A1 * | 3/2018 | Sullivan | A61F 2/90 |

* cited by examiner

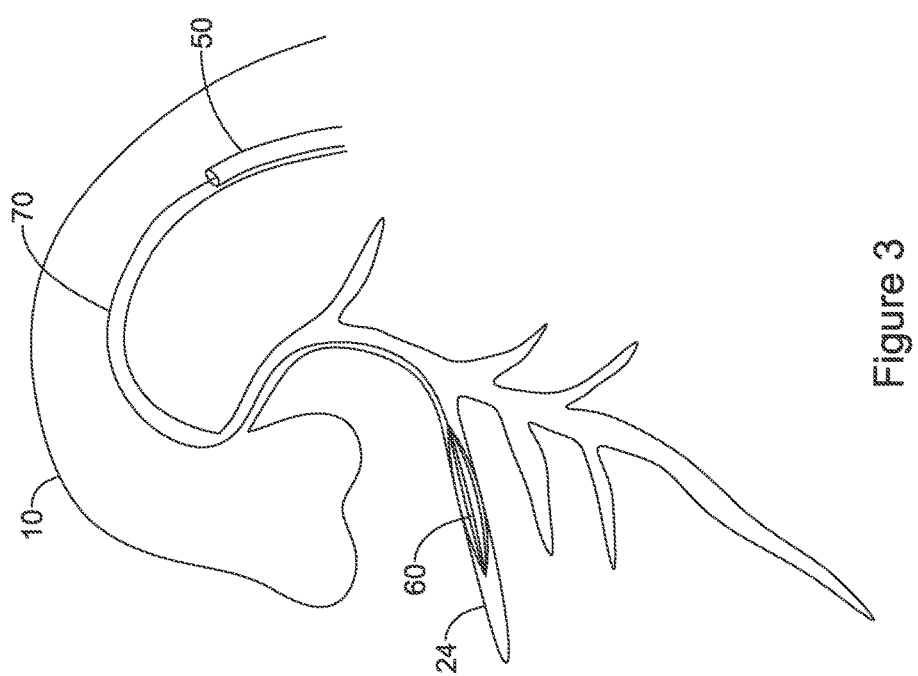

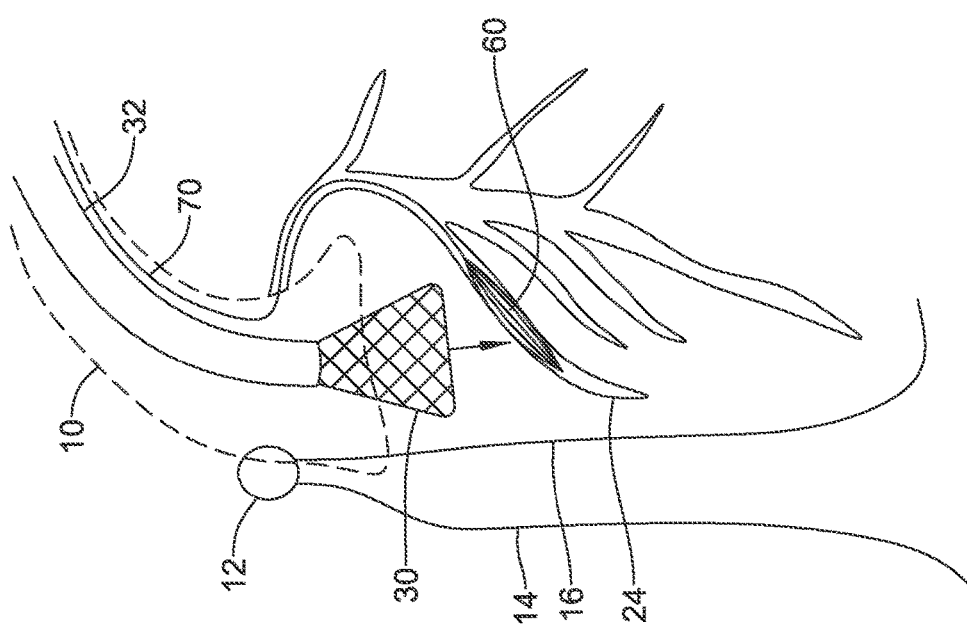

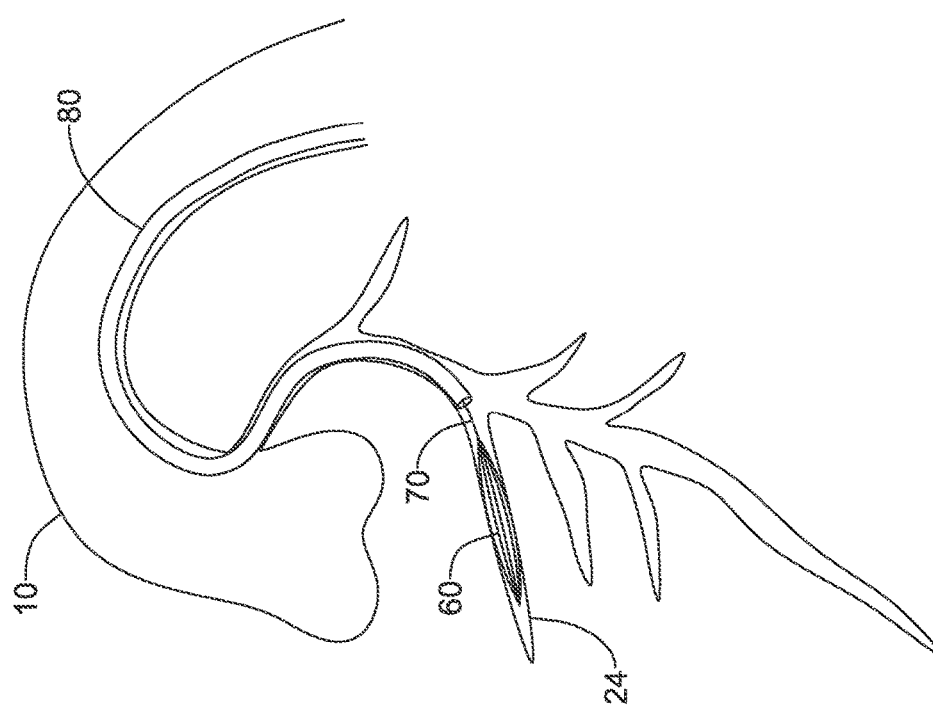

APPARATUS AND METHOD FOR MAINTAINING PATENCY IN A VESSEL ADJACENT TO NEARBY SURGERY

CROSS-REFERENCE TO RELATED APPLICATIONS

This application claims the benefit of priority to U.S. Provisional Application Ser. No. 62/361,655, filed Jul. 13, 2016, the entirety of which is incorporated herein by reference.

BACKGROUND

In the course of surgical interventions, particularly within the heart, the necessary insertion and manipulation of instruments and prostheses may apply pressure to adjacent structures which, when major blood vessels are located within those structures, may result in temporary partial or complete blockage of the vessels and an attendant risk of tissue damage.

For example during the transcatheter positioning of a replacement aortic valve, displacement of the native valve and/or the expansion of components of the replacement valve may incidentally apply pressure to adjacent cardiac wall tissue and thus to the vessels associated with that tissue. In the instance of aortic valve replacement, pressure may be transmitted to the left anterior descending (LAD) branch of the left coronary artery and in particular to the first septal branch of the LAD which supplies the anterior and superior critical portion of the interventricular conduction system. The blood supply to the left anterior fascicle is narrow and the fascicle is susceptible to ischemic damage and possible conduction disturbances. Damage, if it occurs, may be transient or permanent and may not be immediately apparent.

While stents, including temporary stents and steerable deployment/retrieval systems therefor are known in the art, those stents are deployed in an occluded or partially occluded coronary artery or other vessel and rely for their utility, in part, upon expansion to a diameter greater than the diameter of the vessel and/or an occluding deposit prior to introduction of the stent, the over-expansion being necessary to increase the patency of the vessel in which the stent is to be deployed.

Accordingly, a need exists for methods and appropriate apparatus for preventing, or at least minimizing, restriction of blood flow in the vicinity of surgical interventions.

SUMMARY

In certain aspects, this disclosure pertains to an apparatus for maintaining patency of a non-occluded coronary artery during nearby surgery comprising a retrievable patency maintaining element having a first compact configuration and a second expanded configuration, wherein in the second expanded configuration the retrievable patency maintaining element is sized and adapted to maintain patency of a non-occluded coronary artery while contacting opposed walls of the non-occluded coronary artery without significantly altering a diameter of the non-occluded coronary artery and further wherein the retrievable patency maintaining element is configured and adapted to sufficiently resist external collapsing forces which may be applied to the non-occluded coronary artery during nearby surgery such that patency is maintained; a steerable delivery catheter having a distal lumen sized and adapted to receive the retrievable patency maintaining element in the first compact configuration and to release the retrievable patency maintaining element within the non-occluded coronary artery; and a retrieval mechanism for the retrievable patency maintaining element.

In addition or alternatively invention relates to a method of preserving patency in a non-occluded coronary artery during nearby surgery comprising advancing a steerable delivery catheter having a retrievable patency maintaining element contained therein in a first compact configuration into an non-occluded coronary artery within a patient within which coronary artery patency is to be preserved; deploying the retrievable patency maintaining element in the non-occluded coronary artery, withdrawing the steerable delivery catheter a predetermined distance from the non-occluded coronary artery within which patency is to be preserved; performing surgery nearby the non-occluded coronary artery within which patency is to be preserved; retrieving the retrievable patency maintaining element from the non-occluded coronary artery using a retrieval mechanism for the retrievable patency maintaining element; and removing the retrieval mechanism for the retrievable patency maintaining element from the patient.

BRIEF DESCRIPTION OF DRAWINGS

FIG. 3 illustrates an aspect of use of the invention.

FIG. 5 illustrates schematically the function of an implanted temporarily implanted stent of the invention.

FIG. 6 illustrates an aspect of use of the invention.

DETAILED DESCRIPTION

Figure 1:
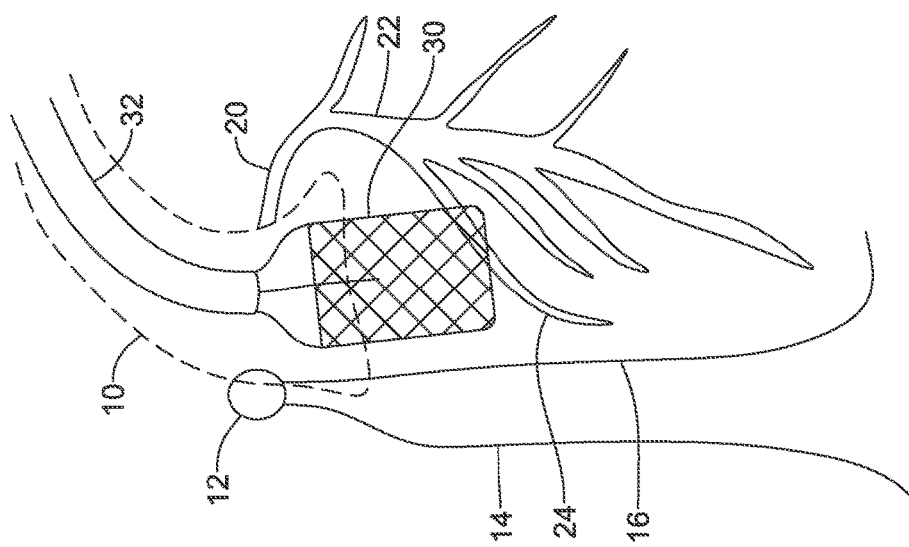
FIG. 1, illustrates schematically the relationships between the aortic valve and a vessel to be protected against undesirable compression. Throughout the figures, heart tissue has been largely omitted or indicated in phantom for clarity.

The following description should be read with reference to the drawings wherein like reference numerals indicate like elements throughout the several views. The drawings, which are not necessarily to scale, are not intended to limit the scope of the claimed invention. The detailed description and drawings illustrate exemplary aspects of the claimed invention.

Although some suitable dimensions, ranges and/or values pertaining to various components, features and/or specifications are disclosed, one of skill in the art, informed by the present disclosure, would understand that desired dimensions, ranges and/or values may deviate from those expressly disclosed unless the context clearly indicates an intended limitation.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an aspect", "some aspects", "other aspects", etc., indicate that the aspect described may include a particular feature, structure, or characteristic, but every aspect may not necessarily include the particular feature, structure, or characteristic. Moreover, such phrases are not necessarily referring to the same aspect. Further, when a particular feature, structure, or characteristic is described in connection with an aspect, it would be within the knowledge of one skilled in the art to effect such feature, structure, or characteristic in connection with other aspects whether or not explicitly described unless clearly stated to the contrary.

For example, the apparatus described herein comprises a steerable delivery catheter, a retrievable patency maintaining element, and a retrieval mechanism for the retrievable patency maintaining element, each of which may be provided in any of several alternative forms. It would be unnecessarily repetitious to attempt to recite each possible combination of the elements suited to provide the respective functions of the claimed elements. Instead, it will be understood that the claimed apparatus comprises a steerable delivery catheter selected from a group of steerable delivery catheters; a retrievable patency maintaining element selected from a group of retrievable patency maintaining elements; and a retrieval mechanism for the retrievable patency maintaining element selected from a group of retrieval mechanisms for the retrievable patency maintaining elements, wherein the steerable delivery catheter is adapted to deliver the selected retrievable patency maintaining element and the retrieval mechanism is adapted to retrieve the selected retrievable patency maintaining element. It will also be understood that the retrieval mechanism may, or may not, be the same as the steerable delivery catheter.

The apparatus of the claims will be described with reference to its use during the implantation of a transcatheter aortic valve replacement and with reference to the utility of the apparatus in maintaining patency of a coronary artery, in particular a non-occluded first septal branch, located in the vicinity of the aorta which might otherwise be adversely compressed during the procedure. FIG. 1 illustrates, somewhat schematically, the implantation of a replacement aortic heart valve using a transcatheter approach. In the figure, the majority of the coronary tissue has been omitted to more clearly show the relative positions of the pertinent structures which include the aorta 10, the atrioventricular node (AV node) 12, the right bundle branch (RBB) 14, the left bundle branch (LBB) 16, the left coronary artery 20, the left anterior descending (LAD) artery 22, and the first septal branch 24 thereof. In addition, the figure illustrates an initial placement of a Transcatheter Aortic Valve Replacement (TAVR) device 30 and the delivery catheter 32 for the TAVR device. Although the intervening tissue has been omitted, it will be seen that the TAVR device may be juxtaposed with the arterial pathway defined by the first septal branch 24 such that incidental contact between the TAVR device 30 and the heart wall may tend to compress the first septal branch 24. Such compression may temporarily restrict or block blood flow through the narrow first septal branch 24 with possible ischemic damage to the septum, the left anterior fascicle and to the anterior and superior critical portion of the interventricular conduction system with possible conduction disturbances. The damage may be transient or permanent. One of ordinary skill in the art is capable of assessing proposed surgical procedures with regard to likelihood that tissue compression around the surgical site will spread from the surgical site and with regard to the risk of damage from temporary compression of tissue around the surgical site and thus will be able to evaluate the term "nearby" as used herein.

Figure 2:
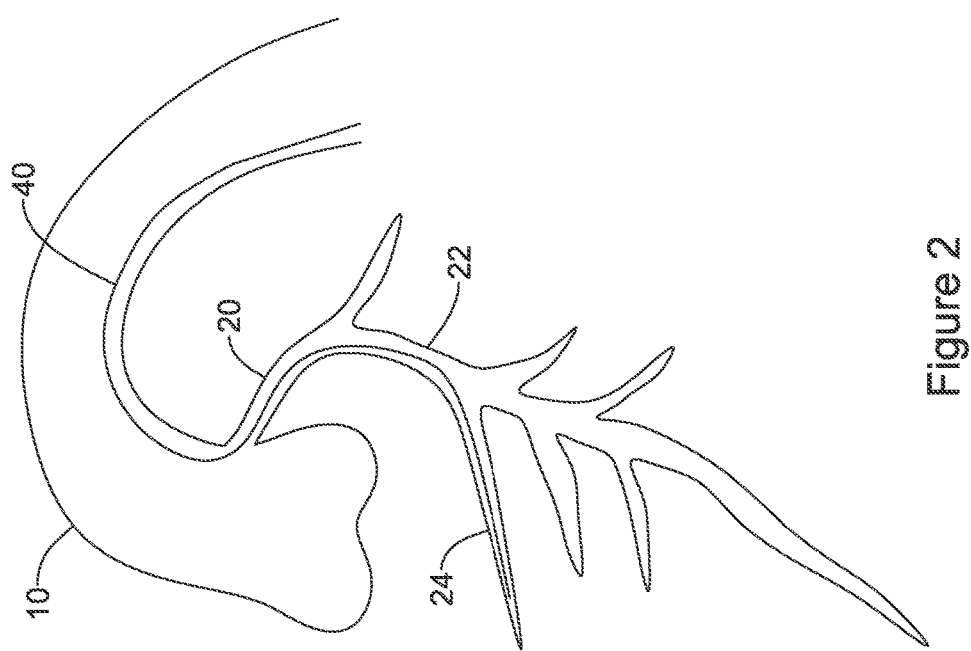
FIG. 2 illustrates the placement of a guidewire.
Figure 4A:
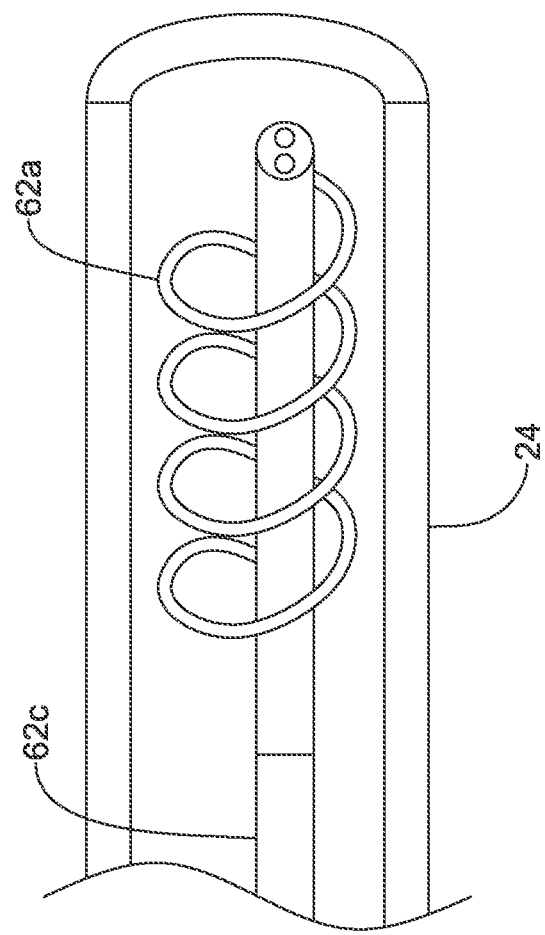
FIGS. 4A-4E illustrate exemplary, non-limiting forms of retrievable patency maintaining elements.
Figure 4B:
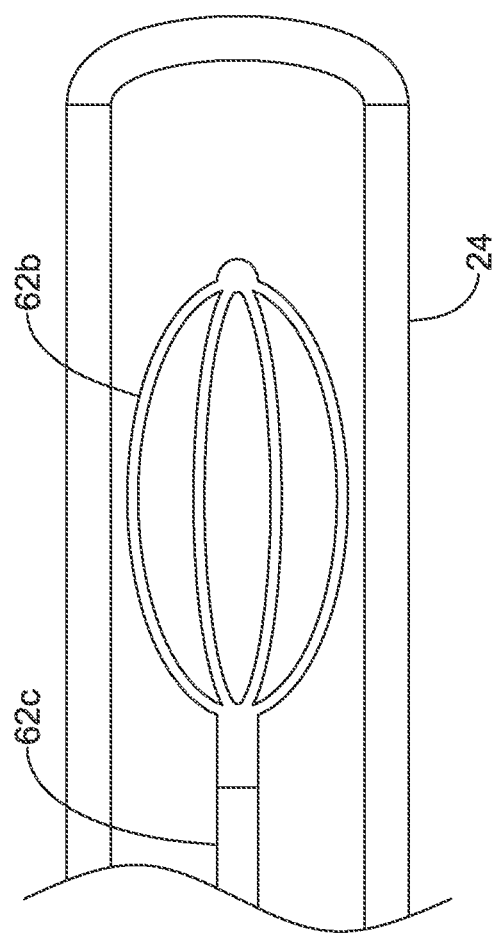
Figure 4C:
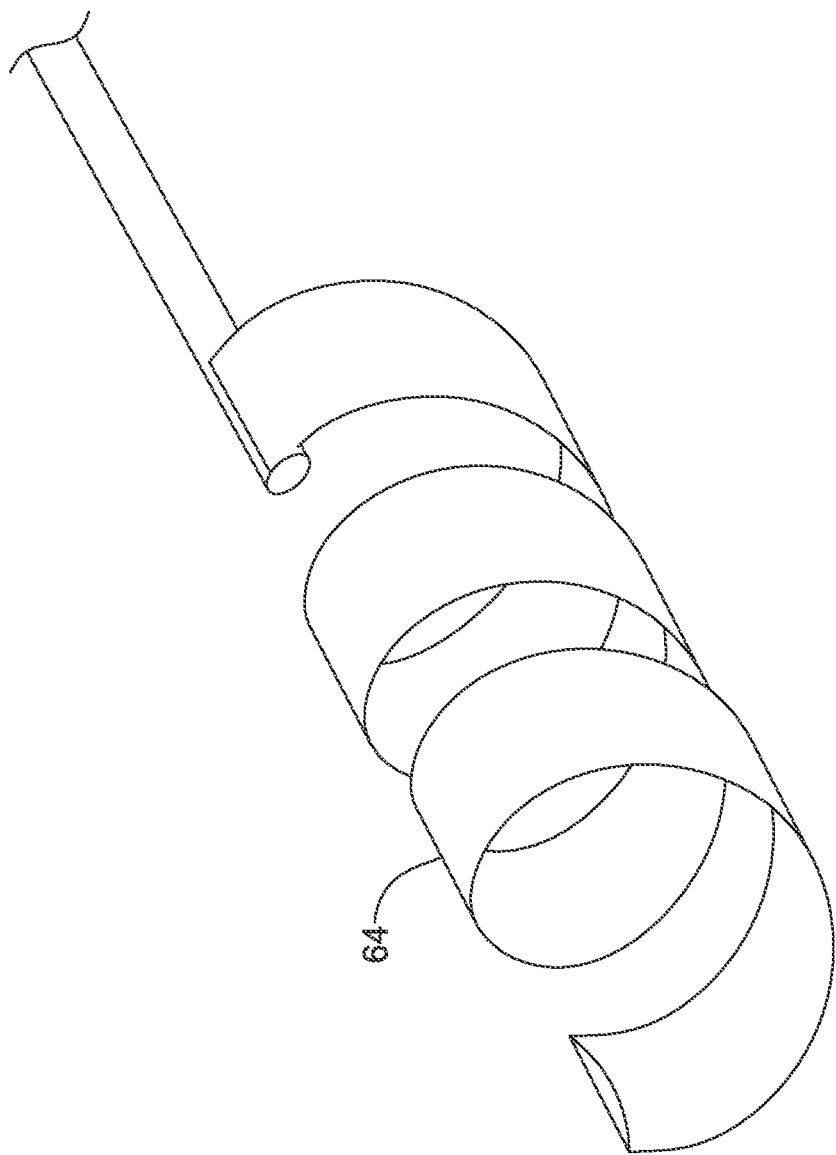
Figure 4D:
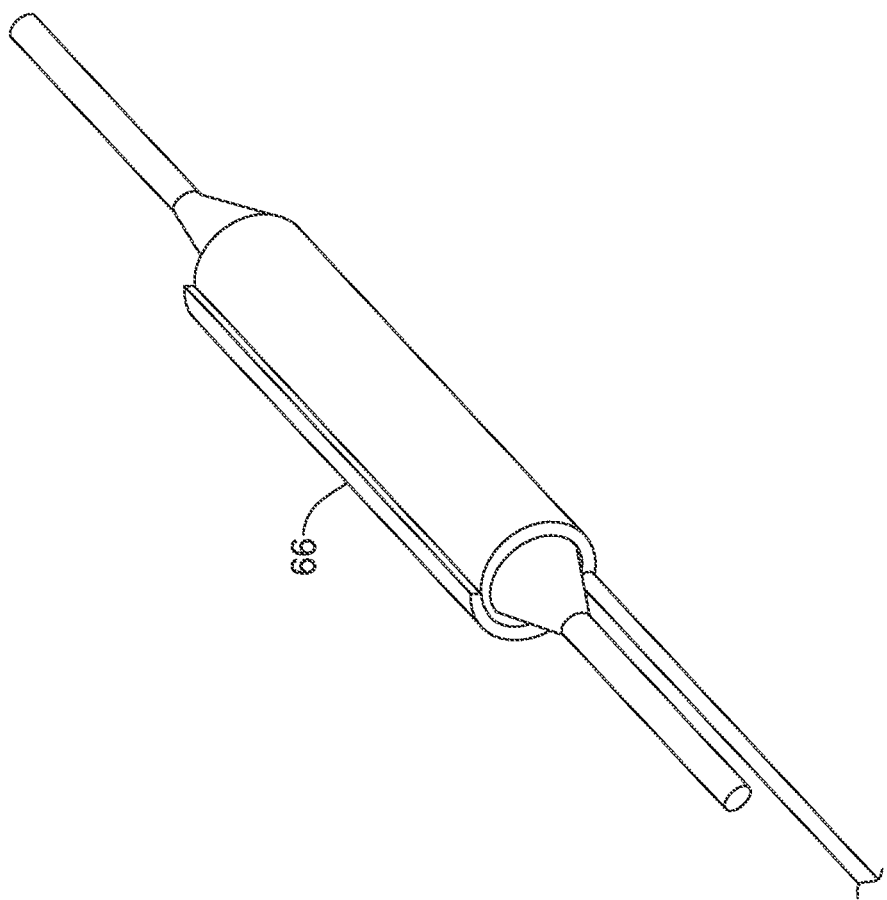
Figure 4E:
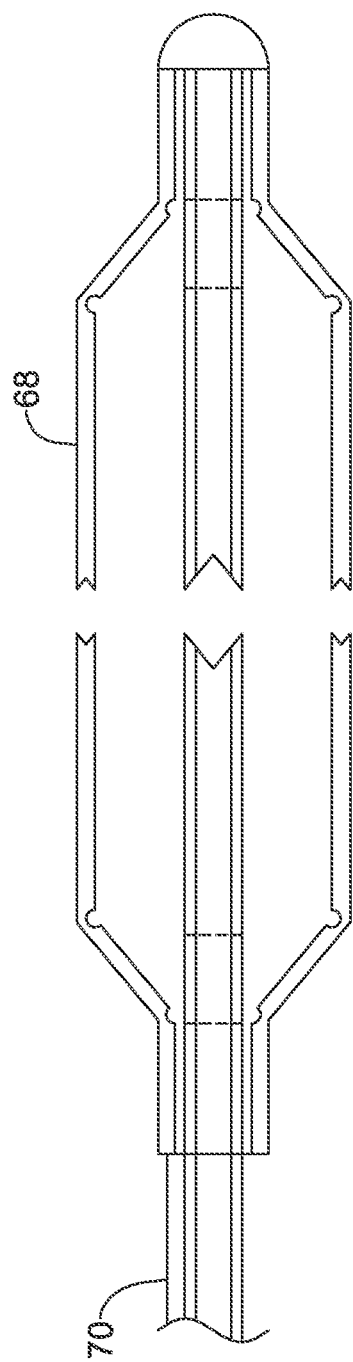

In a non-limiting example of an apparatus of the invention and its use, a steerable delivery catheter 50 containing a retrievable patency maintaining element 60 in a first compact configuration may be steered to a non-occluded artery to be protected by being advanced over a guidewire 40 which has previously been advanced through an aorta 10 into a left coronary artery 20 and into a non-occluded first septal branch 24 of a left anterior descending artery 22 (FIGS. 2 and 3). Once the steerable delivery catheter 50 has been positioned within the non-occluded first septal branch 24, a retrievable patency maintaining element 60 of, for example, a type illustrated in FIG. 4A-E may be deployed from a first compact configuration within the distal end of the steerable delivery catheter 50 into the non-occluded first septal branch 24, and there may assume a second expanded configuration when deployed within the non-occluded first septal branch 24. If desired, the steerable delivery catheter 50 may be withdrawn a predetermined distance (as shown in FIG. 3) to a less crowded portion of the aorta 10 or even removed from the patient. In this aspect of the invention, the retrievable patency maintaining element 60 has attached thereto a wire tether 70 which remains accessible to the operator. In some alternate aspects of the invention the steerable deliver catheter 50 may be of sufficiently small cross-section that it may remain within the coronary arteries during a surgical procedure. In other aspects, the retrievable patency maintaining element 60 may be completely detached from the steerable delivery catheter 50.

At this point, a surgical procedure, such as the implantation of a transcatheter aortic valve replacement, may be carried out in the conventional manner. The close proximity of aortic annulus to the ventricular conduction system and the susceptibility of the first septal branch 24 to inadvertent compression due to mechanical interactions before during and after prosthesis implantation, may lead to restricted blood flow and possible ischemic damage to the left anterior fascicle and/or left posterior fascicle with resultant conduction disturbances which may be transient or permanent. The retrievable patency maintaining element 60 resists collapsing forces directed toward the protected artery thereby preventing some or all of the potential ischemic damage to the conduction pathways.

Following the surgical procedure, a retrieval mechanism 80, which may be the steerable delivery catheter 50 or a may be a separate device, is advanced to the retrievable patency maintaining element 60, either directly or over a tether element 70, if present, whereupon the retrievable patency maintaining element 60, may be engaged and removed. Engagement of the retrievable patency maintaining element 60 by the retrieval mechanism 80 may, in some aspects, include withdrawing the retrievable patency maintaining element 60 at least partially within the distal end of the retrieval mechanism 80.

In a further non-limiting example of an apparatus of the invention and its use, a steerable delivery catheter 50 containing a retrievable patency maintaining element 60 in a first compact configuration may be steered to a non-occluded artery, e.g., first septal branch 24 to be protected, by employing a steerable delivery catheter 50 of the type including a flexible tip and one or more push or pull wires. Once the steerable delivery catheter 50 has reached the non-occluded first septal branch 24, a retrievable patency maintaining element 60 of the type illustrated in, for example, FIG. 4A may be deployed within the non-occluded first septal branch 24 by withdrawing the steerable delivery catheter 50, whereupon the retrievable patency maintaining element 60 expands or is expanded to a diameter not more than 10% greater than the nominal diameter of the non-occluded first septal branch 24 prior to the insertion of the retrievable patency maintaining element 60. The steerable delivery catheter 50 may then be further withdrawn a predetermined distance (See FIG. 3) thereby largely clearing the field near the aortic valve so that the implantation of a transcatheter aortic valve replacement device 30, may be carried out in the conventional manner.

As may be seen in FIG. 5, the presence of a retrievable patency maintaining element 60 within first septal branch 24, or other susceptible vessel, reduces or prevents obstruction of the vessel by compression of tissue adjacent to a site of incidental compression of coronary tissue near the non-occluded first septal branch 24 will be resisted, thereby maintaining patency of the non-occluded first septal branch 24.

A steerable delivery catheter 50 of the invention may be actively steered or may be passively steered by being advanced along a previously positioned guidewire 40. An actively steered catheter may, for example, be of the type including a flexible tip and one or more push or pull wires (exemplified by U.S. Pat. No. 5,906,590); of the type including a plurality of thermally activated deflection elements (exemplified by U.S. Pat. No. 4,601,705); of the type employing rotation of a rigid torsional element, such as a bent guidewire, to direct the curved distal end selectively (exemplified by U.S. Pat. No. 4,545,390); and of the type employing electroactive polymers (exemplified by U.S. Pat. No. 7,951,186), each incorporated by reference, among others known in the art.

A suitable retrievable patency maintaining element 60 generally has the form of a temporarily implantable stent of the art which has been adapted for the current purpose by limiting the degree of expansion such that the stent may contact the walls of the unobstructed coronary artery in which it is deployed without significantly altering the diameter of the artery. One of ordinary skill in the art will appreciate that an artery is not significantly altered if the diameter increase is limited to no more than 0%, 1%, 2%, 4%, or 10%. The retrievable patency maintaining element 60 is adapted and configured for the current purpose by the choice of materials and or the inclusion of structure which resists deformation of the retrievable patency maintaining element 60 when external vessel collapsing forces are applied to the region of the vessel containing the retrievable patency maintaining element 60. Structural modifications may include bridging elements which employ tension and/or compression to preserve the generally cylindrical shape of the retrievable patency maintaining element 60.

Non-limiting examples of suitable retrievable patency maintaining elements 60 include a helical balloon 62A (see FIG. 4A), exemplified in U.S. Pat. No. 7,766,871; an inflatable balloon cage 62B (see FIG. 4B), the balloons optionally including a check-valve (not shown) and a detachable inflation lumen 62C; a helical ribbon coil 64 (FIG. 4C), exemplified in, for example, U.S. Pat. No. 6,027,516; a coiled sheet 66 (FIG. 4D), exemplified in, for example, U.S. Pat. No. 6,027,516; an expandable slotted tube 68 (FIG. 4E), exemplified in, for example, U.S. Pat. No. 6,013,019. Other devices such as expandable wire or polymeric braids may also be used. Suitable retrievable patency maintaining elements 60 may be self-expanding or may be actuated to attain their expanded configuration in a conventional manner.

In some aspects, a retrievable patency maintaining element 60 is released within the coronary artery to be protected and held in position by one or more wall engaging features (not shown). In other aspects, a retrieval mechanism 80 may engage a proximal portion of the retrievable patency maintaining element 60 to allow it to be pulled within the retrieval mechanism 80 or may suitably elongate the retrievable patency maintaining element 60 thereby reducing its diameter to allow its removal. In certain aspects, the retrievable patency maintaining element 60 has attached thereto a tether 70 which facilitates retrieval of the retrievable patency maintaining element 60 by guiding a retrieval mechanism 80 to the retrievable patency maintaining element 60 and providing a tensile force adapted to pull the retrievable patency maintaining element 60 within the distal end of the retrieval mechanism 80 or allowing the retrieval mechanism 80 to be advanced over the retrievable patency maintaining element 60. Any of a variety of engagement mechanisms known in the art may be used.

A tether 70, if present, may also serve to maintain the position of the retrievable patency maintaining element 60 within the coronary artery during the surgical procedure. Tether(s) 70, if present may be, for example, a suture, a braid, or a wire.

In yet other aspects, a retrieval mechanism 80 adapted to function with a balloon retrievable patency maintaining element 60 may include a check-valve release or other balloon deflating feature. As noted previously, in certain aspects, the steerable delivery catheter 50 may be configured and adapted to serve as a retrieval mechanism 80.

GLOSSARY OF ELEMENTS OF THE DRAWINGS

10 Aorta
12 Atrioventricular node (AV node)
16 Left bundle branch (LBB)
20 Left coronary artery
22 Left anterior descending (LAD) artery
24 First septal branch artery
30 Transcatheter Aortic Valve Replacement device (TAVR)
32 TAVR device delivery catheter
40 Guidewire
50 Steerable delivery catheter
60 Retrievable patency maintaining element
62A-68 Variations of retrievable patency maintaining element 60
70 Tether
80 Retrieval mechanism In certain aspects, this disclosure pertains to an apparatus for maintaining patency of a non-occluded coronary artery during nearby surgery comprising a retrievable patency maintaining element having a first compact configuration and a second expanded configuration, wherein in the second expanded configuration the retrievable patency maintaining element is sized and adapted to maintain patency of a non-occluded coronary artery while contacting opposed walls of the non-occluded coronary artery without significantly altering a diameter of the non-occluded coronary artery and further wherein the retrievable patency maintaining element is configured and adapted to sufficiently resist external collapsing forces which may be applied to the non-occluded coronary artery during nearby surgery such that patency is maintained; a steerable delivery catheter having a distal lumen sized and adapted to receive the retrievable patency maintaining element in the first compact configuration and to release the retrievable patency maintaining element within the non-occluded coronary artery; and a retrieval mechanism for the retrievable patency maintaining element.

In addition or alternatively the invention relates to an apparatus, wherein the steerable delivery catheter employs an initially positioned guidewire which serves to steer the steerable delivery catheter to a deployment site.

In addition or alternatively the invention relates to an apparatus, wherein the steerable delivery catheter employs a catheter which has a deflectable tip.

In addition or alternatively the invention relates to an apparatus, wherein the steerable delivery catheter and the retrieval mechanism are the same catheter.

In addition or alternatively the invention relates to an apparatus, wherein the steerable delivery catheter and the retrieval mechanism are different catheters.

In addition or alternatively the invention relates to an apparatus, wherein the retrievable patency maintaining element maintains a connection to the steerable delivery catheter during the nearby surgery.

In addition or alternatively the invention relates to an apparatus, wherein the retrievable patency maintaining element maintains a connection to the steerable delivery catheter through at least one of a tether, an activation link, and an inflation tube.

In addition or alternatively the invention relates to an apparatus, wherein the tether or the activation link is a suture, a braid, or a wire.

In addition or alternatively the invention relates to an apparatus, wherein the retrievable patency maintaining element maintains a connection to the retrieval mechanism during the nearby surgery.

In addition or alternatively the invention relates to an apparatus, wherein the retrievable patency maintaining element maintains a connection to the retrieval mechanism through at least one of a tether, an activation link, and an inflation tube.

In addition or alternatively the invention relates to an apparatus, wherein the tether or the activation link is a suture, a braid, or a wire.

In addition or alternatively the invention relates to an apparatus, wherein retrievable patency maintaining element is an inflatable element which includes a check valve.

In addition or alternatively the invention relates to an apparatus, wherein retrievable patency maintaining element is an expandable helical wire stent.

In addition or alternatively the invention relates to an apparatus, wherein retrievable patency maintaining element is an expandable laser cut tubular stent.

In addition or alternatively the invention relates to an apparatus, wherein retrievable patency maintaining element is an initially coiled sheet of an elastomeric material.

In addition or alternatively the invention relates to an apparatus for maintaining patency of a non-occluded coronary artery during nearby surgery comprising a retrievable patency maintaining element having a first compact configuration and a second expanded configuration, wherein in the second expanded configuration the retrievable patency maintaining element is sized and adapted to maintain patency of a non-occluded coronary artery while contacting opposed walls of the non-occluded coronary artery without significantly altering a diameter of the non-occluded coronary artery and further wherein the retrievable patency maintaining element is configured and adapted to sufficiently resist external collapsing forces which may be applied to the non-occluded coronary artery during nearby surgery such that patency is maintained; a steerable delivery catheter having a distal lumen sized and adapted to receive the retrievable patency maintaining element in the first compact configuration and to release the retrievable patency maintaining element within the non-occluded coronary artery; and a retrieval mechanism for the retrievable patency maintaining element.

In addition or alternatively the invention relates to an apparatus, wherein the retrievable patency maintaining element maintains a connection to the retrieval mechanism during the nearby surgery.

In addition or alternatively the invention relates to an apparatus, wherein the retrievable patency maintaining element maintains a connection to the retrieval mechanism through at least one of a tether, an activation link, and an inflation tube.

In addition or alternatively the invention relates to an apparatus, wherein the tether or the activation link is a suture, a braid, or a wire.

In addition or alternatively the invention relates to an apparatus, wherein the inflation tube includes a valve adapted to control flow of fluid during inflation, an implantation interval, and/or deflation of the retrievable patency maintaining element.

In addition or alternatively the invention relates to an apparatus, wherein the retrievable patency maintaining element is expanded from the first compact configuration to the second expanded configuration by at least one of relative motion between the tether and the steerable delivery catheter; relative motion between the activation link and the steerable delivery catheter; and introduction of a fluid through the inflation tube and a valve.

In addition or alternatively the invention relates to an apparatus, wherein the retrievable patency maintaining element is self-expanding from the first compact configuration to the second expanded configuration.

In addition or alternatively the invention relates to an apparatus, wherein the retrievable patency maintaining element is formed from a shape memory material.

In addition or alternatively the invention relates to an apparatus, wherein the shape memory material is Nitinol.

In addition or alternatively the invention relates to an apparatus, wherein the retrievable patency maintaining element is a balloon.

In addition or alternatively the invention relates to an apparatus, wherein the retrievable patency maintaining element is a collapsible cage-like structure.

In addition or alternatively the invention relates to an apparatus, wherein the steerable delivery catheter includes the retrieval mechanism for the retrievable patency maintaining element.

In addition or alternatively the invention relates to a method of preserving patency in a non-occluded coronary artery during nearby surgery comprising advancing a steerable delivery catheter having a retrievable patency maintaining element contained therein in a first compact configuration into an non-occluded coronary artery within a patient within which coronary artery patency is to be preserved; deploying the retrievable patency maintaining element in the non-occluded coronary artery, withdrawing the steerable delivery catheter a predetermined distance from the non-occluded coronary artery within which patency is to be preserved; performing surgery nearby the non-occluded coronary artery within which patency is to be preserved; retrieving the retrievable patency maintaining element from the non-occluded coronary artery using a retrieval mechanism for the retrievable patency maintaining element; and removing the retrieval mechanism for the retrievable patency maintaining element from the patient.

In addition or alternatively the invention relates to a method of preserving patency in a non-occluded coronary artery during nearby surgery, wherein the withdrawing step further includes maintaining a connection between the retrievable patency maintaining element and the steerable delivery catheter or a retrieval mechanism.

In addition or alternatively the invention relates to a method of preserving patency in a non-occluded coronary artery during nearby surgery, wherein maintaining a connection between the retrievable patency maintaining element and the steerable delivery catheter or a retrieval mechanism is through at least one of a tether, an activation link, and an inflation tube.

In addition or alternatively the invention relates to a method of preserving patency in a non-occluded coronary artery during nearby surgery, wherein the tether or the activation link is a suture, a braid, or a wire.

In addition or alternatively the invention relates to a method of preserving patency in a non-occluded coronary artery during nearby surgery, wherein the inflation tube includes a valve adapted to control flow of a fluid during inflation, an implantation interval, and/or deflation of the retrievable patency maintaining element.

In addition or alternatively the invention relates to a method of preserving patency in a non-occluded coronary artery during nearby surgery, wherein the withdrawing step does not include maintaining contact between the retrievable patency maintaining element and the steerable delivery catheter or a retrieval mechanism.

In addition or alternatively the invention relates to a method of preserving patency in a non-occluded coronary artery during nearby surgery, wherein the retrieving step includes advancing the retrieval mechanism along the connection between the retrievable patency maintaining element and the steerable delivery catheter or a retrieval mechanism.

In addition or alternatively the invention relates to a method of preserving patency in a non-occluded coronary artery during nearby surgery, wherein the retrieving step is performed without relying upon a connection between the retrievable patency maintaining element and the retrieval mechanism.

Although the illustrative examples described above relate to cardiac surgery and in particular to surgery in the vicinity of an aortic valve, the use of the methods and apparatus disclosed in other tissue is also contemplated.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A method of preserving patency in a non-occluded coronary artery during nearby surgery comprising:
   advancing a steerable delivery catheter having a retrievable patency maintaining element contained therein in a first compact configuration into a non-occluded coronary artery within a patient within which coronary artery patency is to be preserved;
   deploying the retrievable patency maintaining element in the non-occluded coronary artery;
   withdrawing the steerable delivery catheter a predetermined distance from the non-occluded coronary artery within which patency is to be preserved;
   performing surgery nearby the non-occluded coronary artery within which patency is to be preserved;
   retrieving the retrievable patency maintaining element from the non-occluded coronary artery using a retrieval mechanism for the retrievable patency maintaining element;
   removing the retrieval mechanism for the retrievable patency maintaining element from the patient wherein the withdrawing step further includes maintaining a connection between the retrievable patency maintaining element and the steerable delivery catheter or a retrieval mechanism; wherein maintaining a connection between the retrievable patency maintaining element and the steerable delivery catheter or a retrieval mechanism is through at least one of a tether, an activation link, and an inflation tube; and wherein the inflation tube includes a valve adapted to control flow of a fluid during inflation, an implantation interval, and/or deflation of the retrievable patency maintaining element.

2. The method of claim 1, wherein the withdrawing step further includes maintaining a connection between the retrievable patency maintaining element and the steerable delivery catheter or the retrieval mechanism.

3. The method of claim 2, wherein maintaining a connection between the retrievable patency maintaining element and the steerable delivery catheter or the retrieval mechanism is through at least one of a tether, an activation link, and an inflation tube.

4. The method of claim 1, wherein the withdrawing step does not include maintaining contact between the retrievable patency maintaining element and the steerable delivery catheter or the retrieval mechanism.

5. The method of claim 1, wherein the retrieving step includes advancing the retrieval mechanism along the connection between the retrievable patency maintaining element and the steerable delivery catheter or a retrieval mechanism.

6. The method of claim 1, wherein the retrieving step is performed without relying upon a connection between the retrievable patency maintaining element and the retrieval mechanism.

* * * * *